United States Patent [19]

Sato et al.

[11] 4,155,946

[45] May 22, 1979

[54] PROCESS FOR DIMERIZING LOWER ALPHA-OLEFINS

[75] Inventors: Hiroshi Sato, Toyonaka; Takanobu Noguchi, Takatsuki; Seimei Yasui, Takarazuka, all of Japan

[73] Assignee: Sumitomo Chemical Company, Limited, Osaka, Japan

[21] Appl. No.: 914,291

[22] Filed: Jun. 9, 1978

[30] Foreign Application Priority Data

Jun. 29, 1977 [JP] Japan .................................. 52-78183
Aug. 29, 1977 [JP] Japan .................................. 52-10391

[51] Int. Cl.$^2$ ............................................. C07C 3/21
[52] U.S. Cl. ................................................. 585/513
[58] Field of Search .............................. 260/683.15 D

[56] References Cited

U.S. PATENT DOCUMENTS

| 3,652,687 | 3/1972 | Bergem et al. | 260/683.15 D |
| 3,803,053 | 4/1974 | Yoo et al. | 260/683.15 D |
| 3,872,026 | 3/1975 | Dunn et al. | 260/683.15 D |

*Primary Examiner*—C. Davis
*Attorney, Agent, or Firm*—Birch, Stewart, Kolasch and Birch

[57] ABSTRACT

A process for dimerizing lower α-olefins using a catalyst comprising (A) at least one nickel compound selected from the group consisting of organic acid salts of nickel, inorganic acid salts of nickel and complexes of nickel, (B) a trialkyl aluminum, (C) at least one phosphorus-containing compound selected from the group consisting of tri-valent phosphorus compounds represented by the formulae: (I) $PR^1R^2R^3$, (II) $(R_2{}^1N)_nPR_{3-n}{}^2$ and (III) $(R^1O)_nPR_{3-n}{}^2$ (in which $R^1$, $R^2$ and $R^3$ are each an alkyl, cycloalkyl, alkenyl, aryl or aralkyl group having up to 18 carbon atoms and n is an integer of 1 to 3), and (D) a halogenated phenol of the formula (IV),

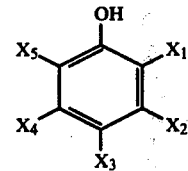

wherein $X_1$, $X_2$, $X_3$, $X_4$ and $X_5$ are each a halogen or hydrogen atom or a hydroxyl group and at least one of them is a halogen atom.

10 Claims, No Drawings

PROCESS FOR DIMERIZING LOWER ALPHA-OLEFINS

The present invention relates to a process for dimerizing lower α-olefins, and more particularly to a process for dimerizing lower α-olefins such as ethylene and propylene using a Ziegler type nickel catalyst.

While polymers such as polyethylene and polypropylene have been produced from lower α-olefins which can be obtained from petroleum abundantly and at a low cost and the production of the polymers takes a basic position in the polymer industries, various dimers having various utilities have also been produced from the lower α-olefins. For instance, among the isomers of the dimer of propylene, 2-methylpentene can be converted into isoprene by a cracking reaction using a silica-alumina catalyst; 4-methylpentene-1 can be converted into polymethylpentene having excellent transparency, electric characteristics and processability by stereoregular polymerization; 2,3-dimethylbutene can be dehydrated to give 2,3-dimethylbutadiene which is useful as a material for synthetic rubbers; and 2,3-dimethylbutene-2 is an important starting material for the preparation of agricultural chemicals or medicines. Furthermore, 3-methylbutene-1, which is a co-dimer of ethylene and propylene, is also useful as a starting material for the preparation of agricultural chemicals or medicines.

The conventional processes for dimerizing lower α-olefins such as propylene are roughly classified into the following four groups.

(1) A process using a cationic catalyst [cf. for example, Terres E., Brönsted Chemie, Vol. 34, page 355 (1953)]:

When this process is applied to dimerization of propylene using phosphoric acid as a catalyst, the dimer is obtained in a very low yield, e.g. up to 20%, while the yield of the trimer or more highly polymerized products reaches 50% or more. Moreover, the dimer consists mainly of 4-methylpentene-2, and other useful isomers can not be obtained in a well-controllable manner.

(2) A process using an anionic catalyst (cf. for example, U.S. Pat. No. 2,986,588):

This process is very superior for obtaining 4-methylpentene-1 with good selectivity, but when the yield of dimers exceeds 30%, the selectivity of 4-methylpentene-1 lowers, and further it is difficult to obtain other isomers in a well-controllable manner.

(3) A process using an alkyl aluminum [cf. for example, Ziegler K., Gellert H. G., Angewandte Chemie, Vol. 64, page 323 (1952)]:

This process is very superior for obtaining 2-methylpentene-1 with good selectivity. The rate of reaction is, however, so late and at the most 15 to 20 g/hr of propylene per 1 g of aluminum is produced, and hence, the catalyst must be used in a high proportion. Moreover, other isomers can not be obtained with good selectivity.

(4) A process using a Ziegler type catalyst containing a transition metal as a main catalyst component:

This catalyst system is superior to the former three ones in terms of the yield of dimers and also the controllability of formation of isomers. A preferred catalyst system contains a nickel compound as a transition metal component. For instance, according to the method disclosed in Japanese Pat. Publication No. 34007/1971, dimerization of propylene is carried out using a catalyst system comprising a π-allyl type nickel complex, an organo-aluminium halide and an organic phosphine to produce propylene dimer in such a high yield as $6 \times 10^3$ g/hr per 1 g of nickel (this is hereinafter represented as "g propylene dimer/g nickel/hr"), and the production of isomrs can also be controlled with very ease. However, this process has still defects that the π-allyl type nickel complex must be synthesized separately by a troublesome means, and further that this complex is very unstable in air and hence is very inconvenient in handling thereof.

Besides, Japanese Pat. Publication No. 30241/1973 discloses a process for dimerizing propylene using a catalyst system comprising a trihalonickelate complex of the formula: $(R_4P)^+(R_3PNiX_3)^-$ and an organoaluminum halide. Japanese Pat. Publication No. 30041/1975 discloses a process for dimerizing propylene using a catalyst system comprising an organic phosphine complex of nickel represented by the formula: $NiX_2 \cdot (PR_3)_2$ and an organo-aluminum halide. In both processes, the complicated nickel complexes must be synthesized separately, so that these processes can hardly be practiced in an industrial scale. Furthermore, a process using a catalyst comprising a nickel compound, an organoaluminum halide and an organic phosphine compound is disclosed in Japanese Pat. Publication Nos. 22807/1972 and 3161/1971 and U.S. Pat. No. 3,513,218. This process provides good results in yield and control of isomers, but use of organoaluminum halides as an organo-aluminum component causes the drawbacks that the halogen atom linked to aluminum is easily separated therefrom and forms a hydrogen halide (HX) which induces serious problems such as corrosion of equipments during operation. Besides the generated HX can not completely be removed by distillation and is unfavorably contaminated into the product. Although the yield of product and the distribution of isomers can be controlled in some degree by changing the number of halogen atoms in organo-aluminum halides, the change of the number of halogen atoms requires an additional reaction step which is not easily carried our during operation.

It is known, on the otherhand, that a catalyst system comprising a nickel compound and a trialkyl aluminum containing no halogen is very low in activity to dimerize propylene or ethylene and requires uneconomical severe reaction conditions such as a reaction temperature of 180° to 250° C. and a reaction pressure of 50 to 150 kg/cm² (cf. Japanese Pat. Publication No. 24431/1964).

In order to eliminate these drawbacks in the known processes, the inventors have extensively studied how to elevate the activity of catalyst systems comprising a nickel compound as a main component and a trialkyl aluminum containing no halogen. As a result, it has surprisingly been found that a catalyst system containing entirely a novel activating agent which can never be analogized from the prior arts displays a high activity to dimerize lower α-olefins and further that the novel catalyst sytem facilitates the control of isomer distribution.

It has also newly been found that while lower α-olefins form generally a dimerized terminal olefin by dimerization, the dimerization of α-olefins and isomerization of the dimeric terminal olefin can be achieved in one step by using the catalyst prepared under specified conditions, and thereby dimeric inner olefins can be produced with a high selectivity.

An object of the present invention is to provide a process for dimerizing lower α-olefins with a catalyst system of which the organo-aluminum component is trialkyl aluminum containing no halogen. Another object of the present invention is to provide a process for dimerizing lower α-olefins with a catalyst system generating no hydrogen halide. A further object of the present invention is to provide a process for obtaining dimeric inner olefins by carrying out dimerization of lower α-olefins and isomerization in one step. These and other objects and advantages of the present invention will become apparent from the following description.

The present invention provides a process for dimerizing lower α-olefins using a catalyst comprising (A) at least one nickel compound selected from the group consisting of organic acid salts of nickel, inorganic acid salts of nickel and complexes of nickel, (B) a trialkyl aluminum, (C) at least one phosphorus-containing compound selected from the group consisting of tri-valent phosphorus compounds represented by the formulae: (I) $PR^1R^2R^3$, (II) $(R_2^1N)_nPR_{3-n}^2$ and (III) $(R^1O)_nPR_{3-n}^2$ wherein $R^1$, $R^2$ and $R^3$ are the same or different and are each an alkyl, cycloalkyl, alkenyl, aryl or aralkyl group having up to 18 carbon atoms and n is an integer of 1 to 3, and (D) a halogenated phenol of the formula (IV):

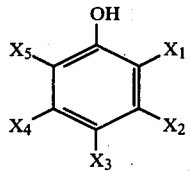

wherein $X_1$, $X_2$, $X_3$, $X_4$ and $X_5$ are the same or different and are each a halogen or hydrogen atom or a hydroxyl group and at least one of them is a halogen atom.

In the present specification, "alkyl" denotes a straight or branched alkyl having 1 to 18 carbon atoms preferably 1 to 12 carbon atoms, such as methyl, ethyl propyl, isopropyl, butyl, tert-butyl, amyl, isoamyl, hexyl, heptyl, octyl, nonyl, decyl, undecyl, dodecyl; "alkenyl" denotes an alkenyl having 2 to 18 carbon atoms, preferably 2 to 12 carbon atoms, such as vinyl, allyl, propenyl, butenyl, pentenyl, hexenyl, heptenyl, octenyl, nonenyl, decenyl, undecenyl, dodecenyl; "cycloalkyl" denotes a cycloalkyl having 3 to 7 carbon atoms, such as cyclopropyl, cyclobutyl, cyclopentyl, cyclohexyl or cycloheptyl; "aryl" denotes a phenyl which may be substituted with one to three alkyl or alkoxy groups having 1 to 3 carbon atoms, such as phenyl, o-, m- or p-tolyl, xylyl, 2,4,6-trimethylphenyl, p-isopropylphenyl, p-methoxyphenyl, o-, m- or p-ethylphenyl, p-ethoxyphenyl; "aralkyl" denotes a phenylalkyl having 1 to 3 carbon atoms in the alkyl moiety, such as benzyl, phenethyl; and "halogen: denotes fluorine, bromine, chlorine and iodine.

The catalyst system of the present invention is very superior, as apparent from the example described hereinafter, in that it has a very high catalytic activity (for example, a high activity of $10^3$–$10^4$ or more g propylene dimer/g nickel/hr), and also in that it facilitates the control of isomer distribution. In comparison with the foregoing prior arts, the technique of the present invention is progressive in the following points: (1) The nickel compound used is an easily available compound and can be prepared without troublesome synthetic technique, and further, it is stable and easy to handle. (2) The organo-aluminum component contains no halogen, and hence, neither generation of hydrogen halide nor corrosion of equipments takes place. (3) Halogenated phenols, which are essential as an activating component of the preent catalyst system, are stable, and halogen atoms linked to the aromatic nucleus are so inactive that they do not react with other catalyst components such as organic aluminum (as shown in examples described hereinafter, a large amount of chlorobenzene is effectively used as a solvent without giving any undesirable effect on the reaction). Since the halogen atoms do not dissociated into an $X^-$ anion, there is no problems such as corrosion of equipments. Bsides, since any hydrogen halide (HX) is not generated, there is no fear of contamination of hydrogen halide into the product. Furthermore, the control of catalytic activity and isomer distribution can easily be carried out by simple operations, for example, by changing the amount of the halogenated phenols or the kind of halogens.

According to the present invention, the nickel catalyst systems containing a trialkyl aluminum and at least one halogenated phenol as an activating agent display a very high catalytic activity in the dimerization of α-olefins. Further, when a tri-valent phosphorus compound of the formulae: (I) $PR^1R^2R^3$, (II) $(R_2^1N)_nPR_{3-n}^2$ and (III) $(R^1O)_nPR_{3-n}^2$, coexists in the catalyst system, there is obtained another characteristic that the control of isomer distribution can easily be carried out.

The active nickel catalyst system of the present invention containing both trialkyl aluminum and halogenated phenols is clearly different from the well-known nickel catalyst systems containing organo-aluminum halide in many points including the co-ordination state or atmosphere of the active components and the electronic state of nickel atom. As shown in the examples described hereinafter, in fact, the catalyst systems containing organo-aluminum halide and those of the present invention produce different isomer distributions from each other even though the same phosphorus-containing compound is used in the two systems.

According to the present invention, by using the catalysts described above, lower α-olefins are dimerized into dimeric terminal olefins having a C—C unsaturated linkage at the end. For example, propylene is dimerized into terminal olefins such as 2,3-dimethylbutene-1 which is a useful intermediate for synthesis of chemicals. The terminal olefins can be isomerized into inner olefins by the well-known methods. For example, 2,3-dimethylbutene-2, which is a useful intermediate for synthesis of agricultural chemicals and the like, can be obtained by isomerization of 2,3-dimethylbutene-1. Further, according to the present invention, isomerized dimers can be obtained in one step with a high selectivity by preparing the catalyst under the specified conditions as described hereinafter. That is, lower α-olefins can be converted directly into dimeric inner olefins. For example, propylene can be converted in one step, with a high selectivity, not into 2,3-dimethylbutene-1 but into 2,3-dimethylbutene-2, which is a isomerized product of the former, under the conditions as described hereinafter.

The present invention will be illustrated in more detail below.

In the present invention, the concentration of catalyst is generally about $10^{-5}$ to about $10^{-1}$ mole (converted to the basis of nickel component) per one liter of reaction system, but it may be optionally changed depending upon the desired reaction rate. The molar ratio of catalyst components is also an important factor for controlling the catalytic activity and isomer distribution. The molar ratios of the components (A), (B), (C) and (D) are not particularly limited, but generally they are within the following ranges: (B)/(A)=2 to 500, preferably 5 to 100 by mole; (C)/(A)=0.1 to 50, preferably 0.5 to 20 by mole; and (D)/(B)=0.2 to 20, preferably 0.5 to 10 by mole. Although the catalytic activity and isomer distribution are delicately affected by the whole components of the catalyst and reaction conditions, generally speaking, the catalytic activity may be increased with increase of the molar ratios of (B)/(A) and (D)/(B), but with increase of the molar ratio of (C)/(A), the activity is decreased. The most suitable molar ratios may properly be selected depending upon the kinds of the desired products.

Among the catalyst components, the phosphorus-containing compound of the catalyst component (C) the most remarkably affects on the distribution of isomeric dimers. Generally speaking, the distribution of isomeric propylene dimers changes from a methylpentenes-rich distribution to a dimethylbutenes-rich distribution with increase of the basicity of phosphorus-containing compounds, while other conditions also affect delicately. The desired selectivity of the isomers can be obtained by selecting the phosphorus-containing compounds according to the required products.

In the present invention, moreover, by selecting the molar ratio of (D)/(B) from the range of 1 to 20, preferably 2 to 10, particularly preferably 2 to 5, inner olefins can selectively be obtained from lower α-olefins in one step via isomerization of the dimers (terminal olefins) of said α-olefins. For example, referring to the dimerization of propylene, the proportion of 2,3-dimethylbutene-2 to the total propylene dimers reaches 50% or more, and under some specific conditions it reaches as high as 80% or more; and further, the proportion of 2,3-dimethylbutene-2 to 2,3-dimethylbutenes reaches 50% or more, and under some specific conditions it reaches as high as 95% or more. On the assumption that all 2,3-dimethylbutene-2 are produced via isomerization of 2,3-dimethylbutene-1, this means that the dimerization and isomerization proceed at the same time almost quantitatively.

In the preparation of the catalyst systems of the present invention, the order for mixing the components is not particularly limited, but generally a preferred order is such that the component (D), halogenated phenol, and the component (B), trialkyl aluminum, are always brought into contact with each other in the presence of the component (A), nickel compound. In other words, it is desirable to avoid such order that the both components (D) and (B) are brought into contact with each other in the absence of the component (A). Specifically preferred mixing orders are as follows: the components (A), (B) and (C) are mixed in an optional order followed by mixing with the component (D); the components (A), (C) and (D) are mixed in an optional order followed by mixing with (B); a mixture of (A) and (B) is mixed with a mixture of (C) and (D); a mixture of (A) and (D) is mixed with a mixture of (B) and (C); and simultaneous mixing of (A), (B), (C) and (D). By the above methods, dimers can be obtained in a high yield.

In the present invention, the catalyst system may previously be prepared in an inert solvent, such as aromatic hydrocarbons (e.g. benzene, toluene and xylene), aliphatic hydrocarbons (e.g. hexane, heptane and cyclohexane), and halogenated aromatic hydrocarbons (e.g. chlorobenzene and o-, m- and p-dichlorobenzene), and then is used for the reaction. Alternatively, the catalyst system may be prepared in a reactor in situ in the presence of the inert solvent, immediately followed by the reaction. Particularly, in order to obtain the catalysts having high uniformity, stability and activity, it is desirable to mix the catalyst components in the presence of α-olefin such as ethylene or propylene. In some cases, the catalysts having an excellent stability can be obtained by mixing the components in the presence of a trace amount of conjugated diene having 4 to 6 carbon atoms, such as butadiene, isoprene or 1,3-pentadiene. The presence of a large amount of conjugated diene in the reaction system somewhat lowers the yield of lower α-olefin dimers, and therefore, the amount of conjugated diene is preferably 1 to 100 times by mole based on the nickel compound.

The dimerization is generally carried out in the inert solvent as described above, but in some cases it may be carried out in a liquefied lower α-olefin such as liquid ethylene or liquid propylene without using any solvent. The reaction temperature is about −50° to about 150° C., preferably about −20° to about 100° C. The reaction is generally carried out under self-generated pressure, 0 to 30 kg/cm$^2$, at a pre-determined temperature. But, in some cases, pressure is applied by means of a compressor.

The lower α-olefins used in the present invention include α-olefins having 1 to 5 carbon atoms such as ethylene, propylene, butene-1, isobutylene and pentene-1. Co-dimerization may be carried out with mixtures thereof, for example a mixture of ethylene and propylene. In the present invention, propylene is particularly preferably used.

The catalyst components used in the present invention are as follows:

(A) The nickel compounds include organic acid salts of nickel, such as nickel naphthenate, nickel octate, nickel formate, nickel acetate, nickel benzoate, nickel oxalate and the like; inorganic acid salts of nickel, such as nickel chloride, nickel bromide, nickel iodide, nickel fluoride, nickel nitrate, nickel sulfate and the like; and complexes of nickel, such as bis-acetylacetonato.nickel, bis-ethylacetoacetato nickel, bis-dimethylglyoximato-nickel and the like.

(B) Trialkyl aluminum includes trimethyl aluminum, triethyl aluminum, tri-n-propyl aluminum, tri-n-butyl aluminum, tri-isobutyl aluminum, tri-n-pentyl aluminum, tri-n-hexyl aluminum, tricyclohexyl aluminum and the like.

(C) The tri-valent phosphorus compounds of the formula (I): $PR^1R^2R^3$ include trimethyl phosphine, triethyl phosphine, tri-n-propyl phosphine, tri-isopropyl phosphine, tri-n-butyl phosphine, tri-isobutyl phosphine, tri-tert-butyl phosphine, tri-n-octyl phosphine, tricyclopropyl phosphine, tricyclohexyl phosphine, triphenyl phosphine, tri-p-tolyl phosphine, tri-p-methoxyphenyl phosphine, tri-(2,4,6-trimethyl)phenyl phosphine, tri-p-isopropylphenyl phosphine, phenyl di-isopropyl phosphine, ethyl di-isopropyl phosphine, methyl di-tert-butyl phosphine, ethyl di-tert-butyl phosphine, ethyl dicyclohexyl phosphine, methyl propyl phenyl phosphine, methyl allyl phenyl phosphine, methyl phenyl benzyl phosphine, and the like.

The amino phosphine compounds of the formula (II): $(R_2^1N)_nPR_{3-n}^2$ include tris-dimethylamino phosphine, tris-diethylamino phosphine, tris-di-n-propylamino phosphine, tris-di-isopropylamino phosphine, tris-di-n- butylamino phosphine, tris-di-isobutylamino phosphine, tris-di-tert-butylamino phosphine, tris-di-cyclohexylamino phosphine, phenyl bis-dimethylamino phosphine, phenyl bis-diethylamino phosphine, phenyl bis-di-n-propylamino phosphine, phenyl bis-di-isopropylamino phosphine, phenyl bis-di-tert-butylamino phosphine, phenyl bis-dicyclohexylamino phosphine, diphenyl diethylamino phosphine, diphenyl di-isopropylamino phosphine, diphenyl di-n-butylamino phosphine, diphenyl di-tert-butylamino phosphine, diphenyl dicyclohexylamino phosphine, ethyl bis-diethylamino phosphine, di-isopropyl diethylamino phosphine, di-isopropyl dibutylamino phosphine, dicyclohexyl di-n-butylamino phosphine, and the like.

The phosphite compounds of the formula (III): $(R^1O)_nPR_{3-n}{}^2$ include trimethyl phosphite, triethyl phosphite, tri-n-propyl phosphite, tri-isopropyl phosphite, tri-n-butyl phosphite, tri-isobutyl phosphite, tri-tert-butyl phosphite, tricyclohexyl phosphite, triphenyl phosphite, tri-p-tolyl phosphite, tri-p-methoxyphenyl phosphite, diethyl phenylphosphinate, di-n-propyl phenylphosphinate, di-isopropyl phenylphosphinate, dicyclohexyl phenylphosphinate, diphenyl phenylphosphinate, and the like.

(D) The halogenated phenol compounds of the formula (IV):

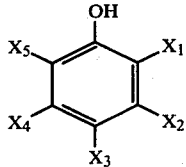

include 2-chlorophenol, 3-chlorophenol, 4-chlorophenol, 2,3-dichlorophenol, 2,4-dichlorophenol, 2,5-dichlorophenol, 2,6-dichlorophenol, 3,4-dichlorophenol, 3,5-dichlorophenol, 2,4,5-trichlorophenol, 2,4,6-trichlorophenol, 2,3,4,6-tetrachlorophenol, pentachlorophenol, 2,3-dichlorohydroquinone, 2,6-dichlorohydroquinone, tetrachlorohydroquinone, 4,6-dichlororesorcinol, 2,4,6-trichlororesorcinol, tetrachlorocatechol and homologues thereof having fluorine, bromine or iodine in place of chlorine. Preferred compounds are those having at least two halogen atoms. Preferred halogen is chlorine atom.

The product is separated from the reaction system by the conventional methods, i.e. by stopping by reaction and removing the catalyst, followed by rectification.

After rectification, the product is further isolated by gas-chromatography, and the composition of the isomers in the product is determined by analyzing the structure by infrared absorption spectrum, nuclear magnetic resonance spectrum and mass analysis.

The present invention will be illustrated by the following examples, which are not however to be interpreted as limiting the present invention thereto.

EXAMPLE 1

A 200-ml Schlenk's tube was deareated, followed by replacement with nitrogen. To the tube were added 20 ml of dry chlorobenzene, 0.75 ml of toluene solution containing 0.15 mmole of nickel naphthenate, 1.5 ml of toluene solution containing 0.15 mmole of triphenyl phosphine and 0.5 ml of isoprene in this order. And, 1.5 ml of toluene solution containing 1.5 mmole of triethyl aluminum was added thereto, followed by stirring at room temperature for 5 minutes. Thereafter, 80 ml of chlorobenzene solution containing 2.25 mmole of 2,4,6-trichlorophenol was added thereto, followed by stirring at room temperature for 10 minutes.

This catalyst solution was charged in a 300-ml stainless steel autoclave with an electromagnetic stirrer of which the atmosphere was previously replaced with nitrogen. After closing the autoclave air-tightly, propylene was charged to a pressure of 5 kg/cm$^2$ and reaction was carried out at 20° C. for 1.5 hours while maintaining the same pressure by supplying propylene. At the initial stage of the reaction, a large quantity of heat was generated, and therefore the autoclave was ice-cooled.

After the reaction was finished, the unreacted propylene was purged, and methanol was added to stop the reaction, followed by washing off the catalyst with water. The product was distilled under atmospheric pressure to recover 55 g of propylene dimer. Catalytic efficiency was $4.2 \times 10^3$ g propylene dimer/g nickel/hr. As a result of analysis by gas-chromatography, the composition of the propylene dimer was as follows: 2-Methylpentene-1 and -2 42%; 4-methylpentene-1 and -2 18%; hexenes 21%, and 2,3-dimethylbutene-1 and -2 20%.

EXAMPLE 2

A 200-ml Schlenk's tube was deareated, followed by replacement with nitrogen. To the tube were added 20 ml of dry chlorobenzene, 0.75 ml of toluene solution containing 0.15 mmole of nickel naphthenate, 1.5 ml of toluene solution containing 0.15 mmole of triisopropyl phosphine and 0.5 ml of isoprene in this order. And, 1.5 ml of toluene solution containing 1.5 mmole of triethyl aluminum was added thereto, followed by stirring at room temperature for 5 minutes. Thereafter, 80 ml of chlorobenzene solution containing 2.25 mmole of pentachlorophenol was added thereto, followed by stirring at room temperature for 10 minutes.

This catalyst solution was charged in a 300-ml stainless steel autoclave of which the atmosphere was previously replaced with nitrogen. After closing the autoclave air-tightly, propylene was charged to a pressure of 5 kg/cm$^2$ and reaction was carried out at 20° C. for 1.5 hours while maintaining the same pressure by supplying propylene. After-treatment and analysis were carried out in the same manner as in Example 1. Thus, 90 g of propylene dimer was obtained.

Catalytic activity was $6.8 \times 10^3$ g propylene dimer/g nickel/hr. The distribution of isomer of the propylene dimer was as follows: 2-Methylpentene-1 and -2 11%; 4-methylpenetene-1 and -2 16%; hexenes 5%; 2,3-dimethylbutene-1 64%; and 2,3-dimethylbutene-2 4.0%.

EXAMPLE 3

Experiment was carried out in the same manner as in Example 2 except that 4.5 mmole of 2,4,6-trichlorophenol was used in place of pentachlorophenol. Thus, 34 g of propylene dimer was obtained. The distribution of isomer of the propylene dimer was as follows: 2-Methylpentene-1 and -2 13%; 4-methylpentene-1 and -2 18%; hexenes 11%; 2,3-dimethylbutene-1 43%; and 2,3-dimethylbutene-2 16%.

EXAMPLE 4

A 200-ml Schlenk's tube was deareated, followed by replacement with nitrogen. To the tube were added 20 ml of dry chlorobenzene, 0.375 ml of toluene solution containing 0.075 mmole of nickel naphthenate, 0.75 ml of toluene solution containing 0.075 mmole of triisopropyl phosphine and 0.5 ml of isoprene in this order. And, 1.5 ml of toluene solution containing 1.5 mmole of triethyl aluminum was added thereto, followed by stirring at room temperature for 5 minutes.

Thereafter, 80 ml of chlorobenzene solution containing 4.5 mmole of 2,4,6-trichlorophenol was added thereto, followed by stirring at room temperature for 10 minutes. This catalyst solution was charged in a 300-ml of stainless steel autoclave of which the atmosphere was previously replaced with nitrogen. After closing the autoclave air-tightly, propylene was charged to a pressure of 5 kg/cm² and reaction was carried out at 20° C. for 1.5 hours while maintaining the same pressure by supplying propylene.

After-treatment and analysis were carried out in the same manner as in Example 1. Thus, 31 g of propylene dimer was obtained.

The distribution of isomer of the propylene dimer was as follows: 2-Methylpentene-1 and -2 17.6%; 4-methylpentene-1 and -2 15.4%; hexenes 8.4%; 2,3-dimethylbutene-1 6.6%; and 2,3-dimethylbutene-2 51%.

EXAMPLE 5

Experiment was carried out in the same manner as in Example 1 except that 1.125 mmole of tetrachloro-p-hydroquinone was used in place of 2,4,6-trichlorophenol. Thus, 30 g of propylene dimer was obtained. The distribution of isomer of the propylene dimer was as follows: 2-Methylpentene-1 and -2 25%; 4-methylpentene-1 and -2 35%; hexenes 23%; 2,3-dimethylbutene-1 16%; and 2,3-dimethylbutene-2 0.5%.

EXAMPLE 6

Experiment was carried out in the same manner as in Example 1 except that 4.5 mmole of pentachlorophenol was used in place of 2,4,6-trichlorophenol. Thus, 25 g of propylene dimer was obtained. The distribution of isomer of the propylene dimer was as follows: 2-Methylpentene-1 and -2 20%; 4-methylpentene-1 and -2 37%; hexenes 20%; 2,3-dimethylbutene-1 19%; and 2,3-dimethylbutene-2 4%.

EXAMPLE 7

A 200 ml Schlenk's tube was deareated, followed by replacement with nitrogen. To the tube were added 20 ml of dry chlorobenzene, 0.15 mmole of bis-acetylacetonato.nickel, 1.5 ml of toluene solution containing 0.15 mmole of triisopropyl phosphine and 0.5 ml of isoprene in this order. And, 1.5 ml of toluene solution containing 1.5 mmole of triethyl aluminum was added thereto, followed by stirring at room temperature for 5 minutes. Thereafter, 80 ml of chlorobenzene solution containing pentachlorophenol of varying amount as shown in Table 1 was added thereto, followed by stirring at room temperature for 10 minutes.

Each catalyst solution was charged in a 300 ml stainless steel autoclave of which the atmosphere was previously replaced with nitrogen. After closing the autoclave air-tightly, propylene was charged to a pressure of 5 kg/cm² and reaction was carried out at 20° C. for 1.5 hours while maintaining the same pressure by supplying propylene. After-treatment and analysis were carried out in the same manner as in Example 1 to obtain the results as shown in Table 1.

Table 1

| | Amount of pentachloro-phenol | Yield of propylene dimer | Composition of dimer (%) | | | | |
|---|---|---|---|---|---|---|---|
| No. | (mmole) | (g) | 2-Methyl-pentene-1 and -2 | 4-Methyl-pentene-1 and -2 | Hexenes | 2,3-Dimethyl-butene-1 | 2,3-Dimethyl-butene-2 |
| 1 | 1.125 | 40 | 12 | 13 | 5.0 | 70 | 0 |
| 2 | 4.5 | 120 | 16 | 20 | 8 | 40 | 16 |

EXAMPLE 8

A 300 ml stainless steel autoclave was deareated, followed by replacement with nitrogen. To the autoclave were added 20 ml of chlorobenzene, 1.5 ml of toluene solution containing 0.15 mmole of nickel naphthenate, and 1.5 ml of toluene solution containing 0.15 mmole of triisopropyl phosphine in this order, and propylene gas was then dissolved therein by bubbling. Immediately thereafter, 1.5 ml of toluene solution containing 1.5 mmole of triethyl aluminum and 80 ml of chlorobenzene solution containing 2.25 mmole of pentachlorophenol were added in this order. After closing the autoclave air-tightly, propylene was charged to a pressure of 5 kg/cm² and reaction was carried out at 40° C. for 1.5 hours while maintaining the same pressure by supplying propylene. After the reaction was finished, after-treatment and analysis were carried out in the same manner as in Example 1. Thus, 60 g of propylene dimer was obtained. The composition of the dimer was as follows: 2-Methylpentene-1 and -2 17.1%; 4-methylpentene-1 and -2 23.9%; hexenes 13.3%; 2,3-dimethylbutene-1 29.9%; and 2,3-dimethylbutene-2 14.8%.

EXAMPLE 9

Experiments were carried out in the same manner as in Example 2 except that the tri-valent phosphorus-containing compounds as shown in Table 2 were used in the same amount in place of 0.15 mmole of triisopropyl phosphine.

Table 2

| | Phosphorous-containing Compound | | Yield of Propylene dimer | Composition of dimer (%) | | | | |
|---|---|---|---|---|---|---|---|---|
| No. | Name | mmole | (g) | 2-Methyl-pentene-1 and -2 | 4-Methyl-pentene-1 and -2 | Hexenes | 2,3-Dimethyl-butene-1 | 2,3-Dimethyl-butene-2 |
| 1 | Tri-n-butyl phosphine | 0.15 | 130 | 38 | 10 | 13 | 35 | 4.0 |
| 2 | Tri-n-octyl phosphine | " | 200 | 35 | 12.5 | 12 | 36 | 4.5 |
| 3 | Tri-p-tolyl phosphine | " | 110 | 46 | 9.0 | 21 | 23 | 2.0 |
| 4 | Tri-p-methoxyphenyl phosphine | " | 105 | 48 | 21.3 | 21 | 4.9 | 4.9 |
| 5 | Tris-dimethylamino phosphine | " | 120 | 42.3 | 26.4 | 14.5 | 13.7 | 3.1 |
| 6 | Tris-di-n-butylamino phosphine | " | 85 | 30 | 20 | 17 | 31 | 2.0 |

Table 2-continued

| No. | Phosphorous-containing Compound Name | mmole | Yield of Propylene dimer (g) | Composition of dimer (%) | | | | |
|---|---|---|---|---|---|---|---|---|
| | | | | 2-Methyl-pentene-1 and -2 | 4-Methyl-pentene-1 and -2 | Hexenes | 2,3-Dimethyl-butene-1 | 2,3-Dimethyl-butene-2 |
| 7 | Tri-n-octyl phosphite | " | 76 | 37 | 15 | 11.8 | 32 | 4.2 |
| 8 | Triphenyl phosphite | " | 90 | 43 | 17 | 11 | 25 | 4.0 |

EXAMPLE 10

Experiments were carried out in the same manner as in Example 2 except that the reaction temperature was changed from 20° C. to 0° C. and 60° C. The results obtained are shown in Table 3.

Table 3

| No. | Reaction temperature (°C.) | Yield of propylene dimer (g) | Composition of dimer (%) | | | | |
|---|---|---|---|---|---|---|---|
| | | | 2-Methyl-pentene-1 and -2 | 4-Methyl-pentene-1 and -2 | Hexenes | 2,3-Dimethyl-butene-1 | 2,3-Dimethyl-butene-2 |
| 25 | 0 | 43 | 10.0 | 13.0 | 5.0 | 70 | 2.0 |
| 26 | 60 | 82 | 17.2 | 20.0 | 13.5 | 10.4 | 45 |

EXAMPLE 11

To a 100 ml Schlenk's tube were added 0.6 mmole of nickel naphthenate (as 3.0 ml of monochlorobenzene solution), 1.2 mmole of triisopropyl phosphine (as 1.0 ml of monochlorobenzene solution) and 0.5 ml of isoprene in this order. And, 6 mmole of triethyl aluminum (as 3.8 ml of monochlorobenzene solution) was added thereto, followed by stirring for 5 minutes. Thereafter, 9 mmol of pentachlorophenol (as 20 ml of monochlorobenzene solution) was added thereto with ice-cooling, followed by stirring for 25 minutes. Thus, a catalyst solution was prepared. After atmosphere in a 9 liter stainless steel autoclave was replaced with nitrogen, 100 ml of dry monochlorobenzene and the above catalyst solution were charged in the autoclave which was then closed air-tightly. Propylene was charged to a pressure of 3–5 kg/cm² and reaction was carried out at 20° C. for 1.5 hours with stirring while maintaining the same pressure by supplying propylene. After the reaction was finished, after-treatment and analysis were carried out in the same manner as in Example 1. Thus, 950 g of propylene dimer was obtained. The content of 2,3-dimethyl-butene-1 of the dimer was 90.5%.

EXAMPLE 12

Experiment was carried out in the same manner as in Example 11 except that 18 mmole of pentachlorophenol was used. Thus, 1100 of propylene dimer was obtained. The distribution of dimer was as follows: 2,3-Dimethyl-butene-1 2.5%; and 2,3-dimethylbutene-2 80.5%.

EXAMPLE 13

To a 200 ml Schlenk's tube, wherein air was replaced with nitrogen, were added 20 ml of dry chlorobenzene, 0.3 ml of toluene solution containing 0.03 mmole of nickel naphthenate, 1.0 ml of toluene solution containing 0.1 mmole of triisopropyl phosphine and 0.5 ml of isoprene in this order. And, 3 ml of toluene solution containing 3.0 mmole of triethyl aluminum was added thereto, followed by stirring at room temperature for 5 minutes. Thereafter, 76 ml of chlorobenzene solution containing 9 mmole of pentachlorophenol was added thereto, followed by stirring at room temperature for 5 minutes. This catalyst solution was charged in a 300 ml stainless steel autoclave of which the atmosphere was previously replaced with nitrogen. After closing the autoclave air-tightly, propylene was charged to a pressure of 5 kg/cm² and reaction was carried out at 20° C. for 1.5 hours while maintaining the same pressure by supplying propylene. At the initial stage of the reaction, generation of a large quantity of heat was observed so that the autoclave was ice-cooled. After the reaction was finished, the unreacted propylene was purged, and methanol was added to stop the reaction. The catalyst components were then washed off with water. The product was distilled under atmospheric pressure to obtain 150 g of propylene dimer. Catalytic efficiency was $5.68 \times 10^4$ g propylene dimer/g nickel/hr. As a result of analysis by gas-chromatography, the composition of the dimer was as follows: Cis- and trans-4-methylpentene-2 20%; 2,3-dimethylbutene-1 4.0%; 2-methylpentene-1 and hexene-1 2.0%; trans-2-hexene 3%; 2-methylpentene-2 10%; cis-hexene-2 2.0%; and 2,3-dimethylbutene-2 61%. From this result, the followings are known: The yield of 2,3-dimethylbutenes is as high as 65%; and isomerization of 2,3-dimethylbutene-1 into 2,3-dimethylbutene-2 is carried out at a high percentage of 94%, which means that the subsequent dimerization and isomerization proceed quantitatively in one step.

EXAMPLE 14

Experiment was carried out in the same manner as in Example 13 except that the amount of triisopropyl phosphine was changed from 0.1 mmole to 0.3 mmole. The yield of propylene dimer was 110 g and catalytic efficiency was $4.17 \times 10^4$ g dimer/g nickel/hr. The composition of the dimer was as follows: Cis- and trans-4-methylpentene-2 20%; 2,3-dimethylbutene-1 3.0%; 2-methylpentene-1 and hexene-1 1.0%; trans-hexene-2 2%; 2-methylpentene-2 11%; cis-hexene-2 1.0%; and 2,3-dimethylbutene-2 60%.

EXAMPLE 15

To a 200 ml Schlenk's tube were added 20 ml of dry chlorobenzene, 0.15 ml of toluene solution containing 0.015 mmole of nickel naphthenate, 0.15 ml of toluene solution containing 0.015 mmole of triisopropyl phosphine, and 0.5 ml of isoprene in this order. And, 1.5 ml of toluene solution containing 1.5 mmole of triethyl aluminum was added thereto, followed by stirring at room temperature for 5 minutes. Thereafter, 78 ml of toluene solution containing 4.5 mmole of pentachlorophenol was added thereto, followed by stirring at room temperature for 5 minutes. This solution was charged in a 300 ml stainless steel autoclave of which the atmosphere was previously replaced with nitrogen. After closing the autoclave air-tightly, propylene was charged to a pressure of 5 kg/cm$^2$ and reaction was carried out at 20° C. for 1.5 hours while maintaining the same pressure by supplying propylene. The reaction mixture was treated in the same manner as in Example 1 to obtain 60 g of propylene dimer. Catalytic efficiency was 4.54×10$^4$ g dimer/g nickel/hr. The composition of the dimer was as follows: Cis- and trans-4-methylpentene-2 30%; 2,3-dimethylbutene-1 2.0%; 2-methylpentene-1 and hexene-1 4.0%; trans-hexene-2 10%; 2-methylpentene-2 18%; cis-hexene-2 4%; and 2,3-dimethylbutene-2 32%.

EXAMPLE 16

Experiments were carried out in the same manner as in Example 13 except that 0.1 mmole each of the trialkyl phosphines and aminophosphines as shown in Table 4 was used in place of triisopropyl phosphine. The results obtained are shown in Table 4.

the same pressure by supplying propylene. The reaction mixture was treated in the same manner as in Example 13 to obtain 110 g of propylene dimer. The composition of the dimer was as follows: n-Hexenes 5%; methylpentenes 27%; and 2,3-dimethylbutenes 68% (composition: 2,3-dimethylbutene-1 4%; and 2,3-dimethylbutene-2 64%).

EXAMPLE 18

Atmosphere in a 200 ml Schlenk's tube was replaced with nitrogen, and 20 ml of dry chlorobenzene, 0.5 ml of toluene solution containing 0.05 mmole of nickel naphthenate, 3 ml of chlorobenzene solution containing 0.3 mmole of triisopropyl phosphine, 0.5 ml of isoprene and 3 ml of toluene solution containing 3 mmole of triethyl aluminum were added thereto in this order. The mixture was stirred at room temperature for 5 minutes. Thereafter, 77 ml of chlorobenzene solution containing pentachlorophenol of an amount as shown in Table 5

Table 4

| No. | Phosphorus-containing compound | Yield of propylene dimer (g) | Composition of dimer (%) | | | Composition of 2,3-dimethylbutenes | | |
|---|---|---|---|---|---|---|---|---|
| | | | 2,3-Dimethyl-butenes | Methyl-pentenes | n-Hexenes | 2,3-Dimethyl-butene-1 | 2,3-Dimethyl-butene-2 | Isomeriza-* tion percentage (%) |
| 1 | Tricyclohexyl phosphine | 160 | 58 | 34 | 8.0 | 4.0 | 96 | 96 |
| 2 | Tri-n-butyl phosphine | 130 | 40.5 | 46.5 | 13 | 3.0 | 97 | 97 |
| 3 | Ethyl di-tert-butyl phosphine | 140 | 50 | 39 | 11 | 5.0 | 95 | 95 |
| 4 | Tris(diethylamino) phosphine | 90 | 35 | 47 | 18 | 4.0 | 96 | 96 |
| 5 | Tris(di-n-butylamino) phosphine | 85 | 41 | 42 | 17 | 5.0 | 95 | 95 |

*) Proportion of 2,3-dimethylbutene-2 to 2,3-dimethylbutenes (%)

EXAMPLE 17

A 200 ml Schlenk's tube was deareated, and 20 ml of dry toluene, 1.5 ml of toluene solution containing 0.15 mmole of nickel naphthenate, 1.5 ml of toluene solution containing 0.15 mmole of triisopropyl phosphine and 0.5 ml of isoprene were added thereto in this order. And, 3.0 ml of toluene solution containing 3.0 mmole of triethyl aluminum was added thereto, followed by stirring at room temperature for 5 minutes. Thereafter, 74 ml of toluene solution containing 9 mmole of pentachlorophenol was added thereto, followed by stirring at room temperature for 5 minutes. This catalyst solution was charged in a 300 ml stainless steel autoclave of which the atmosphere was previously replaced with nitrogen. After closing the autoclave air-tightly, propylene was charged to a pressure of 5 kg/cm$^2$ and reaction was carried out at 20° C. for 1.5 hours while maintaining was added, followed by stirring at room temperature for 5 minutes. This catalyst solution was charged in a 300 ml stainless steel autoclave of which the atmosphere was previously replaced with nitrogen. After closing the autoclave airtightly, propylene was charged to a pressure of 5 kg/cm$^2$ and reaction was carried out at 20° C. for 1.5 hours while maintaining the same pressure by supplying propylene. The reaction mixture was treated in the same manner as in Example 13 to obtain the results as shown in Table 5.

Table 5

| No. | Amount of pentachloro-phenol | | Yield of propylene dimer (g) | Composition of dimer (%) | | | of 2,3-dimethylbutenes | | |
|---|---|---|---|---|---|---|---|---|---|
| | mmole | Molar ratio to Al** | | 2,3-Dimethyl-butenes | Methyl-pentenes | n-Hexenes | 2,3-Dimethyl-butene-1 | 2,3-Dimethyl-butene-2 | Isomeriza-*** tion percentage (%) |
| 1 | 7.5 | 2.5 | 100 | 66 | 29 | 5.0 | 6.0 | 94 | 94 |
| 2 | 9.0 | 3.0 | 110 | 68 | 27 | 5.0 | 4.0 | 96 | 96 |
| 3 | 13.5 | 4.5 | 115 | 65 | 28 | 7.0 | 3.0 | 97 | 97 |

** Molar ratio of pentachlorophenol to triethyl aluminum
*** Proportion of 2,3-dimethylbutene-2 to 2,3-dimethylbutenes (%)

EXAMPLE 19

Experiment was carried out in the same manner as in No. 2 of Example 18 except that 9 mmole each of halogenated phenols as shown in Table 6 was used in place of 9 mmole of pentachlorophenol. The results obtained are shown in Table 6.

Table 5

| No. | Halogenated phenol | Yield of propylene dimer (g) | Composition of dimer (%) 2,3-Dimethyl-butenes | Methyl-pentenes | n-Hexenes | Composition of 2,3-dimethylbutenes 2,3-Dimethyl-butene-1 | 2,3-Dimethyl-butene-2 | Isomerization percentage (%) |
|---|---|---|---|---|---|---|---|---|
| 1 | 2,4,5-Trichloro-phenol | 60 | 67 | 26 | 7.0 | 7.0 | 93 | 93 |
| 2 | 2,4,6-Trichloro-phenol | 65 | 65 | 28 | 7.0 | 6.0 | 94 | 94 |
| 3 | Pentachloro-phenol | 110 | 68 | 26 | 6.0 | 3.0 | 97 | 97 |

EXAMPLE 20

To a 1 liter stainless steel autoclave, wherein air was replaced with nitrogen, were added 40 ml of dry chlorobenzene, 1.5 ml of chlorobenzene solution containing 0.225 mmole of nickel naphthenate, 4.5 ml of chlorobenzene solution containing 0.45 mmole of triisopropyl phosphine, 0.5 ml of isoprene and 4.5 ml of chlorobenzene solution containing 4.5 mmole of triethyl aluminum in this order. The mixture was stirred at room temperature for 5 minutes. Thereafter, 210 ml of chlorobenzene solution containing 13.5 mmole of pentachlorophenol was added thereto, followed by stirring for 5 minutes. After closing the autoclave air-tightly, 270 g of propylene was charged in ten portions (each 27 g) under pressure at 20° C. over 2 hours while stirring by means of an electromagnetic stirrer. After the reaction was finished, the reaction mixture was treated in the same manner as in Example 13 to obtain 260 g of propylene dimer. The yield of the dimer was 96% based on propylene charged. The composition of the dimer was as follows: 2,3-Dimethylbutenes 73%; methylpentenes 24%; and n-hexenes 3%. The composition of 2,3-dimethylbutenes was 97% of 2,3-dimethylbutene-2 and 3% of 2,3-dimethylbutene-1, and isomerization percentage was 97%.

COMPARATIVE EXAMPLE 1

Experiment was carried out in the same manner as in Example 8 except that pentachlorophenol (an activating agent) was not used. The yield of propylene dimer was 3.0 g, which means that catalytic activity is very low.

COMPARATIVE EXAMPLE 2

Experiment was carried out in the same manner as in Example 2 except that 1.5 mmole of ethyl aluminum sesquichloride was used in place of 1.5 mmole of triethyl aluminum and pentachlorophenol was not used. The yield of propylene dimer was 70 g. The composition of the dimer was as follows: 2-Methylpentene-1 and -2 14.5% 4-methylpentene-1 and -2 15.3%; hexenes 28%; 2,3-dimethylbutene-1 59.6%; and 2,3-dimethylbutene-2 4.7%. This distribution of isomer is largely different from that in Example 2, which means that the phosphorus-containing compound acts in a different manner.

COMPARATIVE EXAMPLE 3

To a 200 ml Schlenk's tube were added 20 ml of dry chlorobenzene, 0.3 ml of toluene solution containing 0.03 mmole of nickel naphthenate, 0.3 ml of toluene solution containing 0.3 mmole of triisopropyl phosphine and 0.5 ml of isoprene in this order. Thereafter, 3.0 ml of toluene solution containing 3.0 mmole of ethyl aluminum sesquichloride was added thereto, followed by stirring at room temperature for 5 minutes. This catalyst solution was charged in a 300 ml stainless steel autoclave of which the atmosphere was previously replaced with nitrogen. After closing the autoclave air-tightly, propylene was charged to a pressure of 5 kg/cm² and reaction was carried out at 20° C. for 1.5 hours while maintaining the same pressure by supplying propylene. The reaction mixture was treated in the same manner as in Example 13 to obtain 140 g of propylene dimer. Catalytic efficiency was $5.3 \times 10^4$ g propylene dimer/g nickel/hr. The composition of the dimer was as follows: Cis- and trans-4-methylpentene-2 31%; 2,3-dimethylbutene-1 50%; 2-methylpentene-1 and hexene-1 10%; trans-hexene-2 6%; 2-methylpentene-2 1%; cis-hexene-2 2%; and 2,3-dimethylbutene-2 0%. From this result, it is apparent that isomerization of 2,3-dimethylbutene-1 does not proceed at all. When the results of this Comparative Example 3 are compared with those of Example 14, the effect of halogenated phenol is clearly observed.

What is claimed is

1. A process for dimerizing lower α-olefins using a catalyst comprising (A) at least one nickel compound selected from the group consisting of organic acid salts of nickel, inorganic acid salts of nickel and complexes of nickel, (B) a trialkyl aluminum, (C) at least one phosphorus-containing compound selected from the group consisting of tri-valent phosphorus compounds represented by the formulae: (I) $PR^1R^2R^3$, (II) $(R_2^1N)_nPR_{3-n}^2$ and (III) $(R^1O)_nPR_{3-n}^2$ (in which $R^1$, $R^2$ and $R^3$ are the same or different and are each an alkyl, cycloalkyl, alkenyl, aryl or aralkyl group and n is an integer of 1 to 3), and (D) a halogenated phenol of the formula (IV):

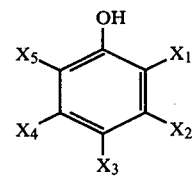

wherein $X_1$, $X_2$, $X_3$, $X_4$ and $X_5$ are the same or different and are each a halogen or hydrogen atom or a hydroxyl group and at least one of them is a halogen atom.

2. A process according to claim 1, wherein the molar ratio of trialkyl aluminum (B)/nickel compound (A) is 2 to 500, that of phosphorus compound (C)/nickel compound (A) is 0.1 to 50 and that of halogenated phenol (D)/trialkyl aluminum (B) is 0.2 to 20.

3. A process according to claim 2, wherein the molar ratio of halogenated phenol (D)/trialkyl aluminum (B) is 0.5 to 10.

4. A process according to claim 2, wherein the molar ratio of halogenated phenol (D)/trialkyl aluminum (B) is 2 to 10.

5. A process according to claim 4, wherein the molar ratio of halogenated phenol (D)/trialkyl aluminum (B) is 2 to 5.

6. A process according to claim 1, wherein said catalyst is prepared by mixing the components (B) and (C) in the presence of the component (A).

7. A process according to claim 1, wherein said catalyst is prepared in the presence of a lower α-olefin.

8. A process according to claim 1, wherein said catalyst is prepared in the presence of a conjugated diene of 1 to 100 mole per 1 mole of nickel compound.

9. A process according to claim 1 or 2, wherein said halogenated phenol is a chlorinated phenol.

10. A process according to claim 1, 2, 4, 6, 7 or 8, wherein said lower α-olefin is propylene.

* * * * *